United States Patent [19]

Vrieland et al.

[11] 4,321,389

[45] Mar. 23, 1982

[54] PROCESS FOR PREPARING 4-BROMO-TETRACHLORO-PYRIDINE

[75] Inventors: G. Edwin Vrieland, Midland, Mich.; Bart J. Bremmer, Ashland, Mass.; Richard E. Crooks, Bay City, Mich.

[73] Assignee: The Dow Chemical Company, Midland, Mich.

[21] Appl. No.: 159,333

[22] Filed: Jun. 16, 1980

Related U.S. Application Data

[63] Continuation-in-part of Ser. No. 95,695, Nov. 19, 1979, abandoned.

[51] Int. Cl.³ ............................................ C07D 213/02
[52] U.S. Cl. .................................................. 546/345
[58] Field of Search ........................................ 546/345

[56] References Cited

U.S. PATENT DOCUMENTS 2,725,402 11/1955 Britton et al. ........................ 260/623

OTHER PUBLICATIONS

Ivashchenko et al., Zh. Obshch. Khim., vol. 39, No. 8, pp. 1695–1697 (1969).
Ivashchenko et al., Chem. Abstracts, vol. 71, No. 25, 124,600f, Dec. 22, 1969.
Den Hertog et al., Rec. Trav. Chim., vol. 70, pp. 353–360, (1951).

*Primary Examiner*—Alan L. Rotman
*Attorney, Agent, or Firm*—Joyce P. Hill; Douglas N. Deline

[57] ABSTRACT

A process for producing 4-bromotetrachloropyridine or symmetrical tetrachloropyridine in high purity comprises the selective transhalogenation of pentachloropyridine by a bromide salt in a polar aprotic solvent at a temperature from about 100° C. to about 140° C. followed optionally by selective debromination by hydrogen in the presence of a noble metal catalyst and an acid acceptor to form tetrachloropyridine.

20 Claims, No Drawings

PROCESS FOR PREPARING 4-BROMO-TETRACHLORO-PYRIDINE

CROSS-REFERENCE TO RELATED APPLICATION

This is a continuation-in-part of copending parent application, Serial No. 95,695, filed Nov. 19, 1979 now abandoned.

BACKGROUND OF THE INVENTION

Chlorinated pyridines and more particularly, symmetrical 2,3,5,6-tetrachloropyridine (hereinafter sym-tetrachloropyridine or s-TCP) are compounds highly valuable as intermediates in the preparation of numerous products having application as agricultural chemicals. The compounds are also directly useful as insecticides or herbicides.

Various methods are known for the preparation of chlorinated pyridines, particularly sym-tetrachloropyridine. These known synthetic methods include the zinc reduction of pentachloropyridine (hereinafter PCP) in U.S. Pat. No. 3,993,654. High conversion of PCP with commercially acceptable selectivity to s-TCP is reported, however, the process consumes large quantities of the expensive zinc and produces a zinc chloride solution that has a potential disposal problem. In addition, the reaction mixture is extremely corrosive.

Several approaches have been attempted which avoid zinc consumption in the catalytic reduction of PCP; however, these processes lack the desired selectivity to s-TCP versus unsymmetrical tetrachloropyridine (hereinafter unsym-TCP) isomers. Generally, catalytic reduction prefers the 2-chlorine, giving primarily the unsym-TCP isomer.

It is desirable to avoid the problems in the prior art processes and yet produce s-TCP in high yields and purity. As will be realized, the tetrachloropyridine product, constituting the subject matter of this invention, minimizes the need for separation techniques which have heretofore been necessary for obtaining s-TCP free from the undesired unsym-TCP isomers. The prior art does not recognize that nearly 100 percent selective replacement of bromine for chlorine in the 4-position of PCP can be obtained under conditions described herein. Neither has it heretofore been recognized that this process for selective production of 4-bromo-2,3,5,6-tetrachloropyridine can be combined with a process for catalytic reduction which prefers bromide over chloride under sufficiently mild conditions to give substantially pure s-TCP.

SUMMARY OF THE INVENTION

It has now been discovered that symetrical 2,3,5,6-tetrachloropyridine can be prepared in high selectivity in a two-step process starting from PCP. First, PCP reacts with a bromide salt in the presence of a polar aprotic organic solvent at temperatures between about 100° C. and about 140° C. The reaction results in the very selective production of 4-bromo-tetrachloropyridine and formation of only minor amounts of 2-bromotetrachloropyridine by-product.

The bromotetrachloropyridine (hereinafter BrTCP) produced may next be reduced by hydrogen over a noble metal catalyst in the presence of a suitable halogen acid acceptor to produce a product having the desired s-TCP in high yield and selectivity.

DETAILED DESCRIPTION OF THE INVENTION

An essential feature of the instant invention is the discovery of the critical importance of the temperature at which the transhalogenation reaction is conducted. At temperatures above about 140° C. the conversion of PCP to BrTCP is higher than the conversion at lower temperatures; however, analysis of the product indicates the presence of a significant quantity, as high as 20 percent or more, of 2-bromotetrachloropyridine. More than 10 percent of 2-bromotetrachloropyridine in the total BrTCP product is generally unacceptable since upon reduction the undesirable unsym-TCP isomer would be produced. It has furthermore been found that the generally used bromide salts become less soluble in the reaction solvents at increasing temperatures thus requiring increasing solvent loads when operating at elevated temperatures.

The minimum reaction temperature is determined by the minimum acceptable reaction rate. Generally, operation at temperatures less than about 100° C. severely reduces the reaction rate. Suitable temperatures are therefore from about 100° C. to about 140° C.; preferably from about 110° C. to about 130° C.

The PCP starting reactant (melting point 124° C.) is known or can be made by methods which are known. The selective bromide exchange with PCP is accomplished by dissolving PCP and a bromide salt in a suitable polar aprotic solvent and heating, with agitation to the desired reaction temperature.

A wide range of bromide salts including the alkali metal bromides, alkaline earth bromides and ammonium bromide may suitably be employed. A preferred group of bromide salts are sodium bromide, potassium bromide, calcium bromide and ammonium bromide. Especially preferred are the salts of sodium and potassium bromide.

Examples of suitable polar, aprotic solvents which may be used for the purpose of this invention are: N,N-dimethylacetamide, N,N-dimethylformamide, N-formylpiperidine, N-formylmorpholine, tetramethylene sulfone and dimethyl sulfoxide. The foregoing solvents are well-known and commercially available.

The halogen exchange reaction appears to be equilibrium limited. That is, the driving force in the reaction is the precipitation of chloride salt by-product, which is desirably less soluble in the reaction medium than is the corresponding bromide salt. However, when equilibrium is reached, a significant amount of unreacted PCP remains dissolved in the reaction medium.

Suitable solvents are selected in order to meet a variety of criteria. The solvent of choice is selected in order to provide good bromide salt and BrTCP solubility in order that the total volume of solvent employed may be kept to a minimum. The solvent is furthermore selected such that the difference in solubility of the bromide and chloride salts is as large as possible in order that the driving force and therefore the equilibrium concentration of s-TCP product is as large as possible. Preferred solvents are N,N-dimethylacetamide and N,N-dimethylformamide.

Typically, operating under the conditions of the instant invention it is possible to obtain conversions of PCP of about 30 to about 60 percent or even more. That is the crude product contains from about 70 to about 40 percent PCP. More importantly however, selectivities of formation of 4-bromotetrachloropyridine based on the ratio of 4-bromotetrachloropyridine formed to PCP converted from about 90 percent to about 99 percent are obtained.

It is not critical to operability of the invention that particular ratios of reactants be utilized since any unreacted materials may be recovered and reused. Suitably, molar ratios of bromide salt:PCP from about 4:1 to about 0.5:1 may be used. Generally in order to avoid large expenses for solvent recycle, saturated solutions of bromide salt and concentrated solutions of PCP are utilized.

The BrTCP formed may be recovered if desired. One method is to add the warm reaction mixture to water or to a mixture of water and an organic solvent such as toluene or perchloroethylene. The chloride and bromide salts present are selectivity extracted in the aqueous phase. The BrTCP products and PCP reactant either precipitate where water alone is employed or are recovered along with the solvent in the organic phase. Purification, if desired, may be accomplished by known methods, for example, fractional distillation, crystallization or liquid chromatography.

The second step of the reaction is the selective catalytic reduction of BrTCP by hydrogen. It has been found that by controlling the reaction conditions it is possible to selectivity reduce the bromine substituent only, producing tetrachloropyridine in very high yields and selectivities.

It has furthermore been discovered that it is not required that BrTCP be recovered and purified after the bromine exchange reaction before the catalytic reduction is performed. In the preferred embodiment the BrTCP for reduction is supplied as the desalinated mixture (hereinafter referred to as crude mixture) obtained from the first step of this reaction process. Accordingly, the bromine exchange product mixture containing solid bromide and chloride salts is filtered and the crude product is reduced by hydrogen in the presence of a noble metal catalyst and an acid acceptor.

The noble metal hydrogenation catalysts that may be used in the practice of this invention include platinum, palladium, rhodium, ruthenium, or mixtures of metals. Platinum or palladium is preferred. The catalyst may be in various forms such as, for example, platinum black, palladium black, ruthenium oxide or rhodium oxide. To reduce the cost of the catalyst and increase its surface area, the noble metal is generally deposited on an inert carrier, such as activated carbon, charcoal, graphite, alumina, silica gel, barium sulfate, or calcium carbonate. Such supported catalysts are well-known in the art. Catalysts that contain from about 0.5 to about 5 percent by weight of the noble metal on the carrier are particularly useful. The amount of the catalyst used is that which will cause the hydrogenation to take place at the desired rate. It is dependent upon such factors as the kind of metal and its surface area. The catalyst may be reused without detrimental results. It will be necessary after a number of reactions that the catalyst be regenerated. This may be accomplished by steam treating or other means as is well-known in the art.

The hydrogen may be provided by an convenient source and preferably is supplied to the reactor as a gas. The hydrogen should be present in at least an amount equal to the equivalents of BrTCP to be reacted. An excess is preferred.

It is important to the success of the reduction reaction that an acid acceptor be utilized in order that the bromide removed from the compound not poison the catalyst. Suitable acid acceptors are organic or inorganic bases including carbonates, bicarbonates, hydroxides, alkoxides, amines, etc., which are stable under the reaction conditions and relatively nonreactive with the catalysts and reactants employed.

The more active acid acceptors such as $Na_2CO_3$ also have been found to promote catalytic activity so that not only is bromine reduced from BrTCP but chlorine is likewise reduced. Operation with such acid acceptors particularly when employing crude mixture is not preferred unless relatively high levels of unsym-TCP, or 4-bromo-trichloropyridine by-products are acceptable. In addition, many generally used acid acceptors such as amine compounds, even relatively unreactive amines such as trialkylamines are not preferred acid acceptors because they may react with one of the reactants or even with the catalyst itself thus reducing reaction rates and yields. However, certain cyclic amine compounds have been found to produce a desirable level of catalytic activity such that bromine is preferentially reduced even when the crude mixture from the first step of the reaction is employed. Preferred acid acceptors particularly for use in reducing crude reaction mixtures are pyridine and $C_{1-4}$ alkyl or monohalo derivatives thereof.

A most preferred acid acceptor is pyridine or a $\beta$-or $\gamma$-substituted $C_{1-4}$ alkyl or monohalo derivative thereof. Utilizing such acid acceptors, extremely low levels of isomeric tetrachloropyridine and tri- and dichloropyridine by-products are produced even using as a reactant the crude reaction product of Step 1.

The acid acceptor is usually employed in an amount corresponding to the chemical equivalent of the hydrogen bromide theoretically obtainable in the reaction, although somewhat greater amounts may be used. Molar ratios of acid acceptor:BrTCP from about 1:1 to about 10:1 are operable.

The debromination reaction is carried out in the liquid phase at moderate temperatures from about 25° C. to about 150° C. Preferred temperatures are from about 30° C. to about 80° C. Pressures are not critical to the success of the invention and may suitably vary from subatmospheric to superatmospheric. Preferred pressures are from about 0.5 atmospheres to about 60 atmospheres, and are easily produced using the $H_2$ gas reactant to supply the pressurizing medium.

Polar solvents are employed such as methanol, ethanol, and the previously named polar aprotic solvents which are already present in the crude reaction product of the first step.

The reaction is conducted by merely contacting the BrTCP with the catalyst in the presence of hydrogen. The presence of other constituents of the crude product of the first step, if such is being reduced, is not detrimental. The reaction may be conducted as a batch process wherein the reactants are combined in a suitable reaction vessel at the desired reaction conditions. Agitation may be provided to ensure contact of the reactants and catalyst. The course of the reaction may be observed by a reduction in pressure due to loss of hydrogen through the reaction.

Separation of the desired reaction product may be accomplished by physically removing the catalyst and any precipitate formed during the reaction and fractionating or selectively crystallizing the remaining components. By the same technique it is possible to purify the resulting tetrachloropyridine product if it is desired to obtain the sym-TCP in greater purity than is produced by the reaction.

The reaction may also be run in a continuous manner by passing hydrogen, the acid acceptor and BrTCP or the crude reaction product through a treatment zone comprising a fixed bed of the noble metal catalyst. Operation in this manner readily permits recycling of reactants and solvent and efficient separation of the catalyst. The tetrachloropyridine product is recovered and purified if desired in the same manner as previously explained.

The following examples illustrate ways in which the principle of the invention has been applied, but are not to be construed as limiting the invention.

EXAMPLES 1-4

Preparation of 4-Bromotetrachloropyridine

In a 250 cc round-bottom glass flask equipped with a reflux condenser and stirrer are placed 20 grams (0.08 mole) of PCP and 100 cc of N,N-dimethylacetamide (DMAC). Varying quantities of sodium bromide as shown in Table I below, are independently added to the PCP-DMAC solution and heated with stirring for 2 hours at the temperatures indicated. The amount of 4-bromotetrachloropyridine, 2-bromotetrachloropyridine and dibrominated product in the reaction product is determined using gas chromatography. From the chromatographs so obtained the percent selectivity is calculated assuming 100 percent accountability of reaction products. The values listed in Table I are these normalized values.

TABLE I

Preparation of 4-BrTCP in High Selectivity

| Example No. | NaBr (g) | Temperature (°C.) | Percent Conversion | % Selectivity 2-Br | 4 Br | dibromo |
|---|---|---|---|---|---|---|
| 1 | 10 | 120 | 39.7 | 1.9 | 96.7 | 1.4 |
| 2 | 20 | 120 | 45.0 | 2.8 | 95.7 | 1.5 |
| 3 | 20 | 140 | 62.3 | 6.8 | 86.1 | 7.5 |
| 4 | 20 | 165 | 65.4 | 20.2 | 59.7 | 20.1 |

The above data reveal that at temperatures above 140° C., higher conversions of PCP to BrTCP are achieved but the converted products contain a larger amount of dibromotrichloropyridine and 2-bromotetrachloropyridine by-products.

EXAMPLE 5

In substantially the same manner as in Examples 1-4, 100 grams of PCP and 100 grams of NaBr are dissolved in 500 cc of DMAC and heated, with stirring, at 118° C. for 3 hours. The resulting reaction product is washed free of NaCl and NaBr with water. The precipitate comprising PCP and BrTCP is dried at 75° C. for several hours with further drying at 100° C. for 6 hours. Analysis of the solid product reveals 46 percent conversion of PCP to BrTCP with 98.5 percent selectivity to 4-bromotetrachloropyridine.

EXAMPLE 6

Debromination

In a 250 ml glass round-bottom flask a mixture of the product of Example 5 containing 2.7 grams of PCP and 2.3 grams of BrTCP was combined in 100 cc of DMAC. The flask was equipped with a sample port, a stirrer, thermometer and hydrogen bubbler. The flask was purged with nitrogen and one gram of a standard 5 percent palladium-on-carbon catalyst (Engelhard #6011) was added. The reaction mixture was heated to 70° C. with stirring while hydrogen was bubbled through the mixture. Samples were withdrawn periodically for analysis by gas chromatography.

The results of the experiment with values calculated as in Table I are contained in Table II.

TABLE II

| Time (hr) | % Conversion BrTCP | Selectivity S-TCP |
|---|---|---|
| 0.5 | 42 | 75 |
| 1.0 | 67 | 80 |
| 1.5 | 74 | 82 |
| 3.0 | 83 | 85 |

By contrast, a similar experiment utilizing only PCP provided a maximum selectivity to s-TCP of only about 30 percent. The selective formation of s-TCP by utilizing BrTCP instead of PCP for the reduction is thus illustrated. However, the failure to achieve high conversions even after long reaction periods indicates that the catalyst becomes poisoned during the course of the reaction due to the HBr formed. It is therefore necessary to employ an acid acceptor.

EXAMPLE 7

Acid Acceptor

The experimental conditions of Example 6 were repeated except that 1 gram of $Na_2CO_3$ acid acceptor was included in the reaction mixture. The results are contained in Table III.

TABLE III

| Time (hr) | % Conversion BrTCP | % Selectivity s-TCP | % Conversion PCP |
|---|---|---|---|
| 0.5 | 50 | 77 | 0 |
| 1.0 | 88 | 74 | 5 |
| 1.5 | approx. 100 | 70 | 16 |
| 2.0 | approx. 100 | 66 | 22 |

It may be seen that use of an acid acceptor prevents poisoning of the catalyst such that conversions approaching 100 percent are achieved very rapidly. It is also noticed that selectivities to s-TCP are not as high as when no acid acceptor is employed. The loss in selectivity is due primarily to the simultaneous catalytic reduction of PCP which tends to predominate during the later stages of the reaction when BrTCP becomes exhausted. This is seen by reference to the percent conversion of PCP, which preferentially dechlorinates primarily at the 2 position to form the unsymmetric isomer. Percent conversions of PCP continue to increase long after the BrTCP has been exhausted resulting in lowered s-TCP selectivities.

EXAMPLE 8

The problem of competing reduction of PCP can be solved by employing a fractionation step prior to the catalytic reduction and thereafter reducing only BrTCP. It would be desirable however to be able to selectively reduce a mixture of PCP and BrTCP to obtain both high conversions of BrTCP and limited simultaneous reduction of PCP. The following acid acceptors were therefore tested for selective debromination.

The experimental conditions of Example 6 were substantially repeated except that various acid acceptors were employed in the place of $Na_2CO_3$. The temperatures and pressures of some reactions were also altered from those of Example 6. Results of these experiments are contained in Table IV. The values obtained were not normalized as in Table I.

TABLE IV

| Acid Acceptor | Reaction Time (hr) | Temp °C. | % Conversion BrTCP | PCP | % Selectivity s-TCP | unsym-TCP |
|---|---|---|---|---|---|---|
| pyridine (2 g) | 1 | 50 | 82 | <2 | 87 | <5 |
|  | 2 | 50 | 98 | <2 | 86 | <5 |
| pyridine (3.9 g) | 1 | 50 | 83 | <2 | 93 | <5 |
|  | 2 | 50 | 98 | <2 | 91 | <5 |
| pyridine* (2 g) | 1 | 25 | 88 | <2 | 91 | <5 |
| α-picoline (2 g) | 1 | 50 | 90 | 3 | 83 | <5 |
|  | 2 | 50 | 100 | 5 | 82 | 6 |
| 2,6-lutidine (2.9 g) | 1 | 50 | 100 | 6 | 85 | 5 |
|  | 2 | 50 | 100 | 16 | 75 | 7** |
| triethylamine | 1 | 50 | 98 | <2 | 74 | 7** |
|  | 2 | 50 | 100 | 24 | 60 | 6** |

*Pressurized with hydrogen to about 2.8 bars.
**Significant amounts of trichloropyridine and other by-products were also produced.

The results shown in Table IV demonstrate the significant influence of pyridine compounds in the selective catalytic reduction of BrTCP in the presence of PCP. In particular it has been found that conversions of BrTCP and catalyst life times can be increased by the presence of a pyridine compound acid acceptors. In addition, the pyridine compounds allowed for the preferential reduction of BrTCP to produce a product high in s-TCP.

What is claimed is:

1. A process for the production of tetrachloropyridine consisting primarily of 2,3,5,6-tetrachloropyridine comprising the steps of
    (a) reacting by contacting pentachloropyridine with a bromide salt selected from alkali metal bromides, alkaline earth bromides, ammonium bromide or mixtures thereof, in the presence of a polar aprotic organic solvent at temperatures between about 100° C. and about 140° C. to form bromotetrachloropyridine-containing crude product; and subsequently
    (b) reducing the bromotetrachloropyridine produced in step (a) by contacting with gaseous hydrogen in the presence of a platinum, palladium, rhodium or ruthenium noble metal catalyst and an acid acceptor.

2. The process of claim 1 wherein the bromide salt is an alkali metal bromide.

3. The process of claim 2 wherein the bromide salt is sodium bromide or potassium bromide.

4. The process of claim 1 wherein the polar aprotic organic solvent is selected from the group consisting of N,N-dimethylacetamide, dimethylformamide, N-formylpiperidine, N-formyl morpholine, tetramethylene sulfone or dimethyl sulfoxide.

5. The process of claim 4 wherein the polar organic solvent is N,N-dimethylacetamide or N,N-dimethylformamide.

6. The process of claim 1 wherein the weight ratios of bromide ion:pentachloropyridine are from 0.5:1.0 to 4.0:1.0.

7. The process of claim 1 wherein the noble metal catalyst is deposited on an inert supporting material.

8. The process of claim 7 wherein the noble metal is platinum or palladium.

9. The process of claim 1 wherein in Step b the bromotetrachloropyridine is selectively reduced in the presence of pentachloropyridine by
    (i) treating the crude product of step (a) to remove precipitate, and subsequently
    (ii) contacting the crude product with hydrogen in the presence of a noble metal catalyst and an acid acceptor; and
    (iii) recovering the tetrachloropyridine produced.

10. The process of claim 9 wherein the bromotetrachloropyridine-containing crude product comprises, in addition to bromotetrachloropyridine, from about 70 percent to about 40 percent pentachloropyridine.

11. The process of claim 10 wherein the acid acceptor is selected from the group consisting of pyridine and monohalo or $C_{1-4}$ monoalkyl or dialkyl derivatives thereof.

12. The process of claim 11 wherein the acid acceptor is pyridine.

13. The process of claim 1 or 9 wherein the molar ratio of acid acceptor:bromotetrachloropyridine is from about 1:1 to about 10:1.

14. The process of claim 1 or 9 wherein the reaction temperature for step (b) is from about 25° C. to about 80° C.

15. A process for the production of a mixture of bromotetrachloropyridine and pentachloropyridine wherein the bromotetrachloropyridine consists essentially of about 90 to about 99 percent of 4-bromotetrachloropyridine comprising
    (a) contacting pentachloropyridine with a bromide salt selected from alkali metal bromides, alkaline earth bromides and ammonium bromide in the presence of a polar aprotic solvent at a temperature from about 100° C. to about 140° C.; and subsequently
    (b) recovering the mixture of bromotetrachloropyridine and pentachloropyridine.

16. The process of claim 15 wherein the bromide salt is an alkali metal bromide.

17. The process of claim 16 wherein the polar aprotic solvent is N,N-dimethylacetamide or N,N-dimethylformamide.

18. The process of claim 17 wherein the reaction temperature is from about 110° C. to about 130° C.

19. The process of claim 17 wherein the mixture is recovered by
    (a) separating the mixture from precipitated salts;
    (b) extracting the mixture to separate inorganic salts; and
    (c) removing the solvent.

20. A process for producing bromotetrachloropyridine wherein
    (a) pentachloropyridine is contacted with a bromide salt selected from alkali metal bromides, alkaline earth bromides and ammonium bromides in the presence of a polar aprotic solvent at a temperature from about 100° C. to about 140° C.;
    (b) recovering a mixture comprising bromotetrachloropyridine and pentachloropyridine; and
    (c) separating the bromotetrachloropyridine from the pentachloropyridine.

* * * * *